(12) United States Patent
Jina

(10) Patent No.: US 7,670,853 B2
(45) Date of Patent: Mar. 2, 2010

(54) ASSAY DEVICE, SYSTEM AND METHOD

(75) Inventor: Arvind N. Jina, San Jose, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 350 days.

(21) Appl. No.: 10/533,350

(22) PCT Filed: Nov. 5, 2003

(86) PCT No.: PCT/US03/35343

§ 371 (c)(1), (2), (4) Date: Nov. 7, 2005

(87) PCT Pub. No.: WO2004/042364

PCT Pub. Date: May 21, 2004

(65) Prior Publication Data

US 2006/0148096 A1    Jul. 6, 2006

Related U.S. Application Data

(60) Provisional application No. 60/424,245, filed on Nov. 5, 2002.

(51) Int. Cl.
*G01N 33/53* (2006.01)

(52) U.S. Cl. .................. 436/514; 436/518; 436/169; 436/172; 436/525; 436/530; 436/805; 436/808; 436/810; 436/66; 436/67; 435/7.1; 435/7.2; 435/7.92; 435/7.94; 435/287.1; 435/287.2

(58) Field of Classification Search ............... 436/514, 436/518, 169, 172, 525, 530, 805, 808, 810, 436/66, 67; 435/7.1, 7.2, 7.92, 287.1, 287.2, 435/7.94
See application file for complete search history.

(56) References Cited

U.S. PATENT DOCUMENTS 4,857,453 A  *  8/1989  Ullman et al. ............. 435/7.92

(Continued)

FOREIGN PATENT DOCUMENTS

WO    WO 00/78210          12/2000
WO    WO 00/78210 A1       12/2000

OTHER PUBLICATIONS

Notification of Transmittal of the International Search Report or the Declaration, International Application No. PCT/US03/35343 for TheraSense, Inc., mailed Aug. 19, 2004, 5 pages.

*Primary Examiner*—Bao-Thuy L Nguyen
(74) *Attorney, Agent, or Firm*—Edward J. Baba; Shweta Chandra; Bozicevic, Field & Francis LLP

(57) ABSTRACT

A system for treating a blood sample (700) having an analyte of interest comprises a strip (200) having a membrane (218), respective portions (216, 220 and 222, or 300) which are provided for receiving the sample, for lysing cells of the sample to liberate hemoglobin, and for capturing glycated hemoglobin. The latter two portions (220 and 222, or 300) of the membrane are treated with lysing and capture agents, respectively. A portion of the strip (214 or 230 or 240) is provided for holding an eluting agent and for releasing the agent upon a release condition. A system for detecting analyte comprises an optical subsystem (550) that is aligned with the strip to provide a signal corresponding to an amount of analyte, and an electronic subsystem (650) for processing the signal (560) to provide a result, such as an amount or percentage of glycated hemoglobin. To use these systems, the user simply applies a small sample (700) to the membrane (218) and closes a door (10) of the detection system over the strip (200) such that the door triggers the release of the eluting agent. No sample pre-treatment is required. The preferably handheld system (100) is a simple and convenient monitoring tool for the user, such as a diabetic patient who must monitor blood glucose on an on-going basis. While the systems are useful in the monitoring of blood glucose, they may be used for treating a sample other than blood and detecting an analyte other than an analyte in blood.

17 Claims, 6 Drawing Sheets

U.S. PATENT DOCUMENTS

| | | | |
|---|---|---|---|
| 5,108,564 A | 4/1992 | Szuminsky et al. | |
| 5,128,015 A | 7/1992 | Szuminsky et al. | |
| 5,206,144 A * | 4/1993 | Zeuthen et al. | 435/7.25 |
| 5,242,842 A | 9/1993 | Sundrehagen | |
| 5,262,305 A | 11/1993 | Heller et al. | |
| 5,264,104 A | 11/1993 | Gregg et al. | |
| 5,320,725 A | 6/1994 | Gregg et al. | |
| 5,356,786 A | 10/1994 | Heller et al. | |
| 5,541,117 A | 7/1996 | Karl et al. | |
| 5,559,041 A * | 9/1996 | Kang et al. | 436/518 |
| 5,593,852 A | 1/1997 | Heller et al. | |
| 5,665,222 A | 9/1997 | Heller et al. | |
| 5,837,546 A | 11/1998 | Allen et al. | |
| 5,846,837 A | 12/1998 | Thym et al. | |
| 5,919,708 A | 7/1999 | Sundrehagen | |
| RE36,268 E | 8/1999 | Szuminsky et al. | |
| 5,945,345 A * | 8/1999 | Blatt et al. | 436/518 |
| 5,972,199 A | 10/1999 | Heller et al. | |
| 6,036,919 A | 3/2000 | Thym et al. | |
| 6,055,060 A | 4/2000 | Bolduan et al. | |
| 6,103,033 A | 8/2000 | Say et al. | |
| 6,120,676 A | 9/2000 | Heller et al. | |
| 6,134,461 A | 10/2000 | Say et al. | |
| 6,143,164 A | 11/2000 | Heller et al. | |
| 6,175,752 B1 | 1/2001 | Say et al. | |
| 6,338,790 B1 | 1/2002 | Feldman et al. | |
| 6,534,324 B1 * | 3/2003 | Zin | 436/518 |
| 6,562,581 B2 * | 5/2003 | Law et al. | 435/14 |
| 6,670,192 B1 | 12/2003 | Galen et al. | |
| 6,677,158 B2 | 1/2004 | Hud et al. | |
| 6,746,582 B2 | 6/2004 | Heller et al. | |
| 6,812,038 B1 * | 11/2004 | Mendel-Hartvig et al. | 436/514 |

* cited by examiner

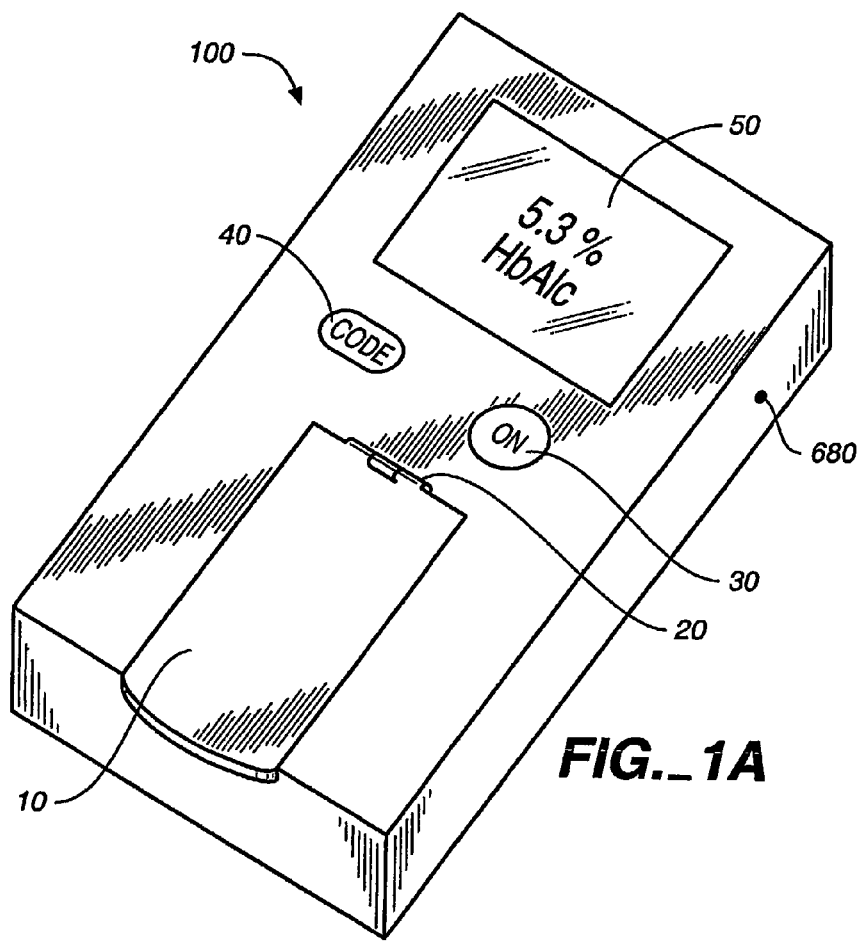
FIG._1A
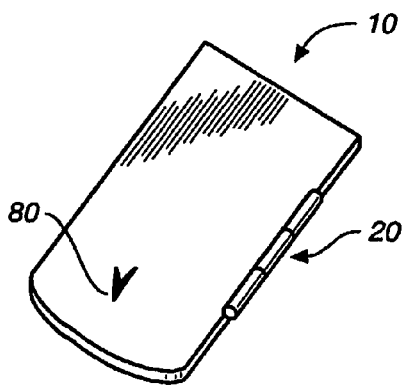
FIG._1B
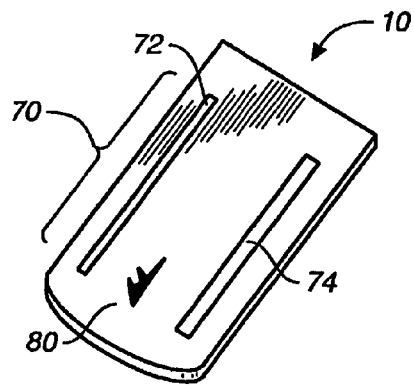
FIG._1C

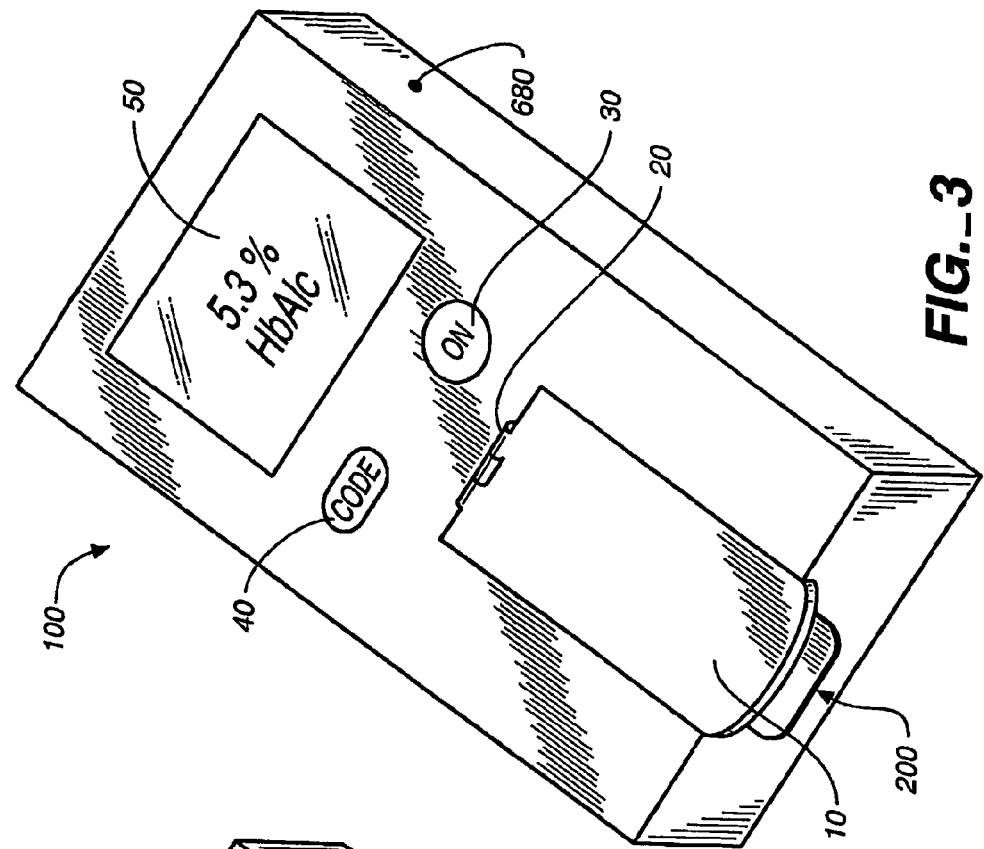
FIG._3
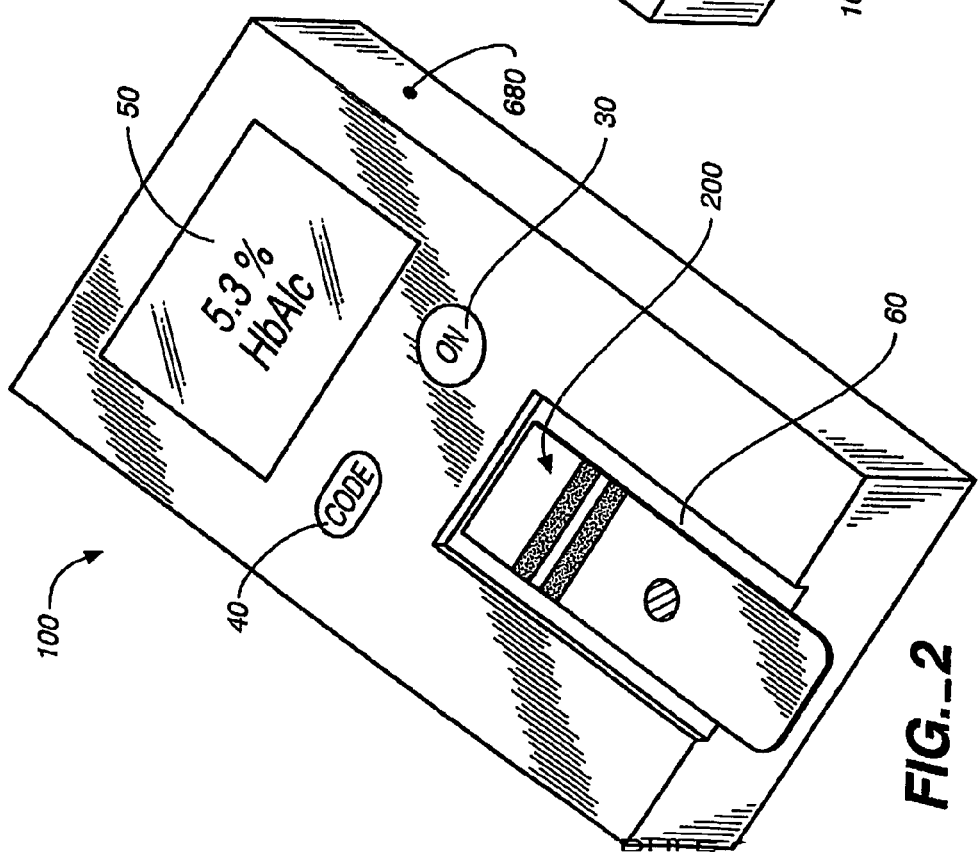
FIG._2

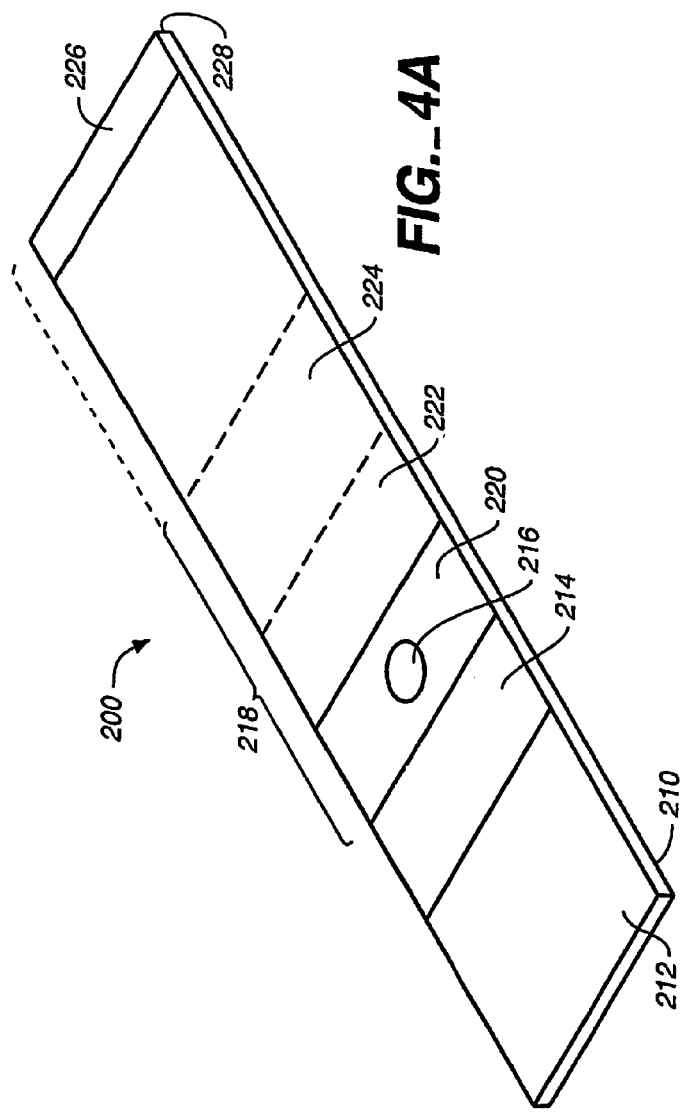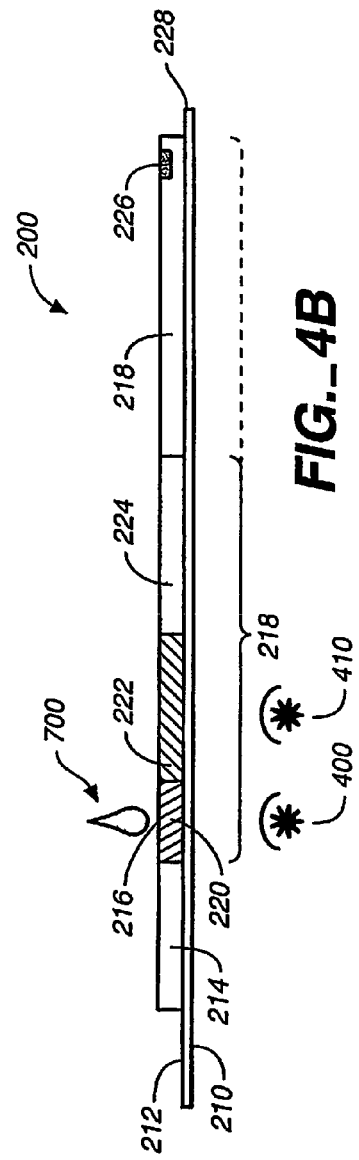

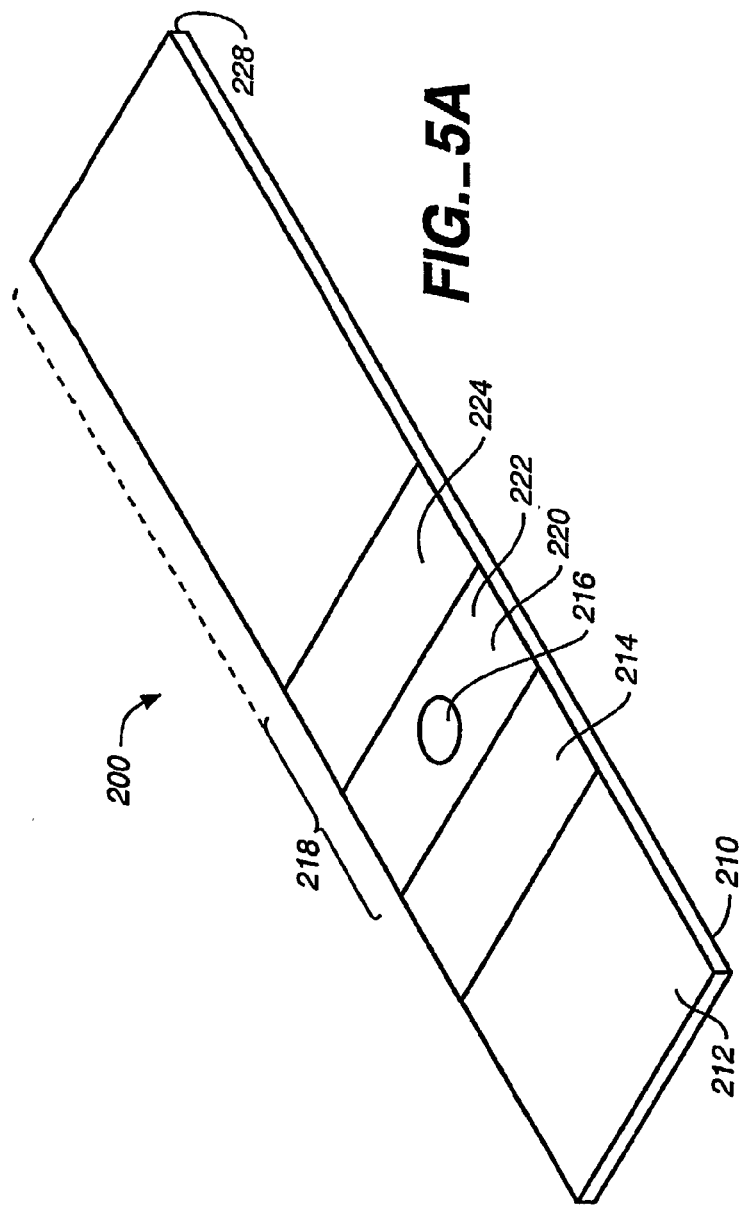
FIG._5A
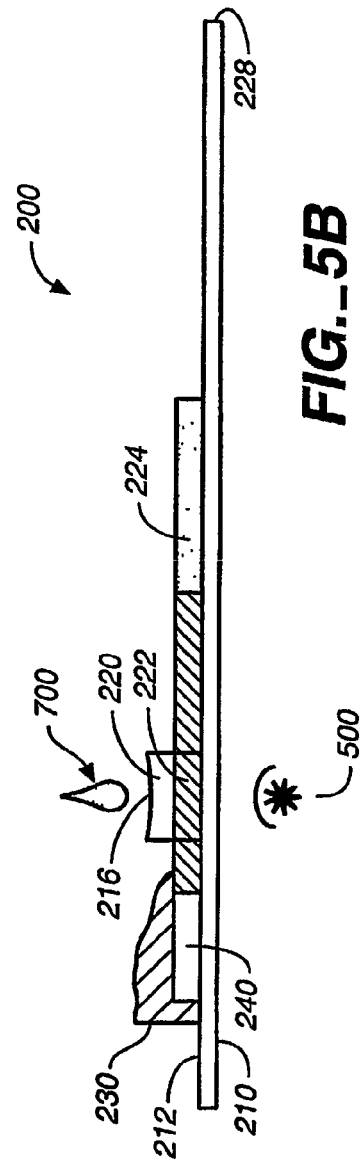
FIG._5B

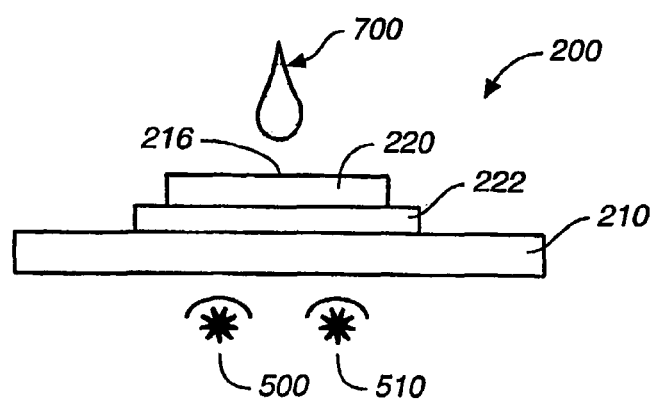
FIG._6
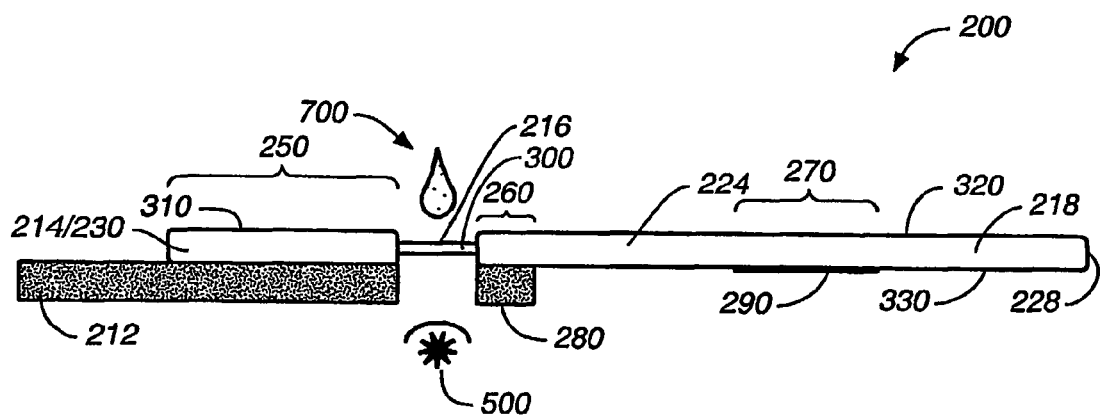
FIG._7

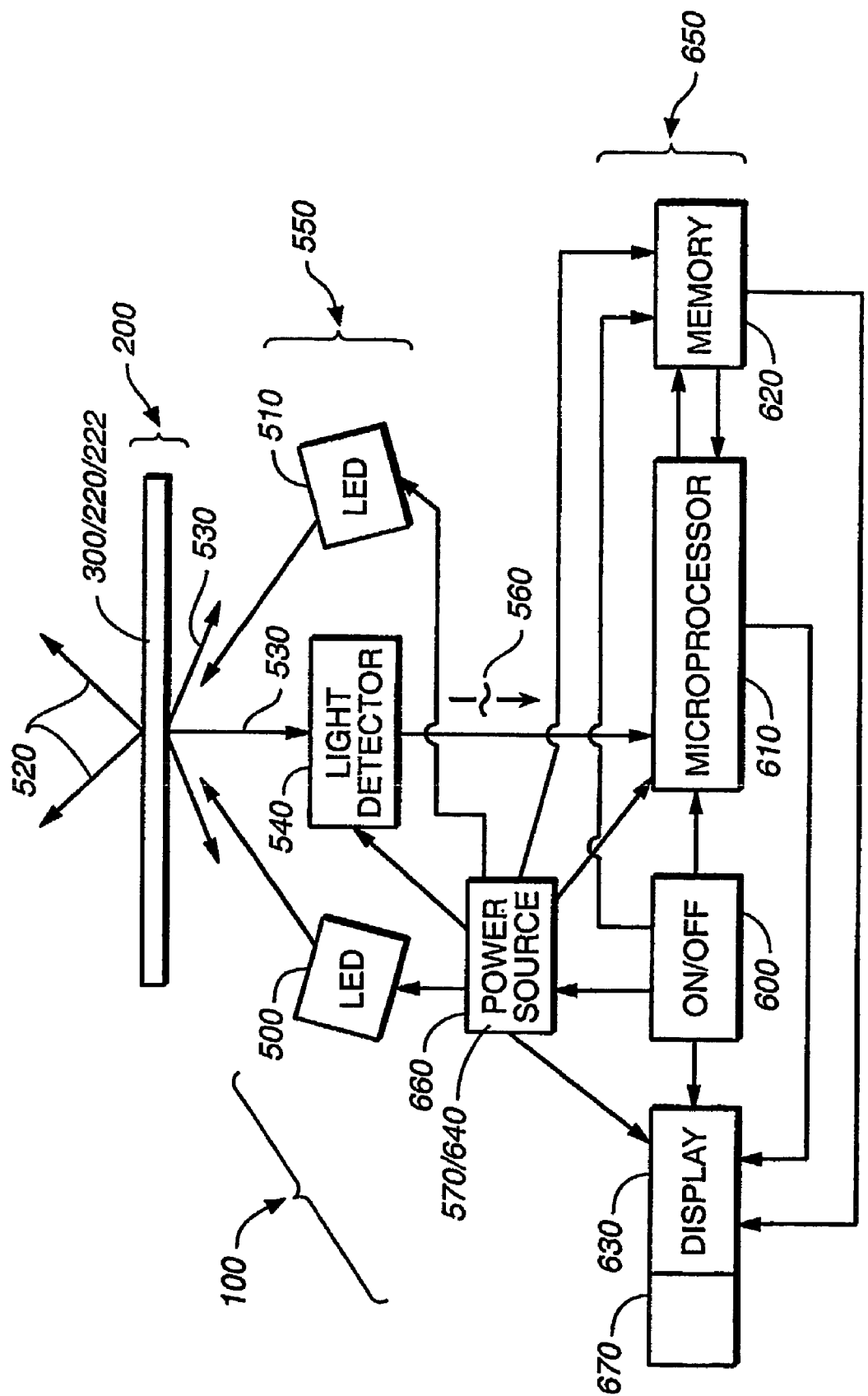
FIG._8

ASSAY DEVICE, SYSTEM AND METHOD

CROSS-REFERENCE TO RELATED APPLICATIONS

This non-provisional application is related to and claims priority based on U.S. Provisional Application No. 60/424,245, entitled "HbA1c Assay System," filed on Nov. 5, 2002, which is incorporated herein in its entirety by this reference. This non-provisional application is also related to U.S. Pat. No. 6,143,164 of Heller et al., entitled "Small Volume In Vitro Analyte Sensor," which issued on Nov. 7, 2000, U.S. Pat. No. 6,338,790 of Feldman et al., entitled "Small Volume In Vitro Analyte Sensor with Diffusible or Non-leachable Redox Mediator," which issued on Jan. 15, 2002, U.S. Pat. No. 6,616,819 of Liamos et al., entitled "Small Volume In Vitro Analyte Sensor and Methods," which issued on Sep. 9, 2003, and U.S. Patent Application Publication No. 2002/0172992 of Heller, entitled "Method for the Determination of Glycated Hemoglobin," which was filed on May 14, 2002, each of which is incorporated herein in its entirety by this reference.

FIELD OF THE INVENTION

This invention generally relates to devices, systems, and methods of detecting an analyte or multiple analytes in a sample, such as a sample from a physiological source. This invention further relates to small, disposable assay devices for detecting an analyte or two or more analytes, such as total hemoglobin and glycated hemoglobin in a blood sample, and providing information, such as a ratiometric value of an amount of glycated hemoglobin relative to an amount of total hemoglobin in a blood sample, based on such detecting of analyte(s), and associated systems and methods.

BACKGROUND OF THE INVENTION

Various systems have been developed for determining the presence of, or the amount of, various analytes in a sample of interest. In a health care context, many such systems, such as systems involving test strips and test meter devices, are simple enough to be used by a person who is not medically trained. For example, such systems have been developed for a person to test blood cholesterol levels, blood glucose levels, urine analytes indicative of pregnancy, such as human chorionic gonadotropin, and the like, in a home setting. An example of a system for use in determining blood glucose levels is the FreeStyle® blood glucose monitoring system available from TheraSense, Inc. of Alameda, Calif. This electrochemical system is particularly advantageous in that a person need only provide a very small sample of blood to obtain a useful and reliable reading of the concentration of glucose in the blood sample.

While it is useful to determine the concentration of glucose in blood, it is particularly useful to determine the amount of irreversibly glycated hemoglobin, or HbA1c, relative to the amount of total hemoglobin, present in a sample of blood. An example of a method for conducting an electrochemical HbA1c assay is set forth in the above-referenced U.S. Patent Application Publication No. 2002/0172992 of Heller. HbA1c refers to glycated hemoglobin formed by a bond between an amine group of hemoglobin and an aldehyde group of glucose, for example, between the amino group of the N-terminal valine of the β-chain of hemoglobin and the aldehyde group of glucose. The binding reaction first forms a Schiff's base and then a stable ketoamine by Amadori rearrangement. The rate of HbA1c formation is directly proportional to the concentration of glucose in the blood. The percentage of HbA1c (i.e., a ratio of the amount of glycated hemoglobin (HbA1c) to the amount of total hemoglobin (Hb) in the blood, multiplied by 100) has come to be taken as a measure of the level of blood glucose control a diabetic has maintained for a period of two or three months prior to the measurement. As such, percentage HbA1c has become an important result by which health care providers can assist diabetics in their care.

Often, it is the health care provider, such as a physician, for example, that is called upon arrange for an assay of a patient's blood to determine HBA1c percentage. In this context, the physician may recognize a need for an HbA1c measurement concerning a patient, such as a diabetic patient, during an office visit. Typically, the physician asks the patient to go to a laboratory to have a blood sample drawn, whereupon the laboratory tests the sample to obtain an HbA1c measurement and provides the physician with the measurement result hours or days after the office visit. Because of the time lag between the office visit and the physician's receipt of the result, the physician typically reviews the result long after the patient has left the office. If the physician believes that further consultation with the patient is required in light of the test result, the patient must be contacted again. This system is not particularly convenient, expedient, or cost-effective.

Thus, a market demand has developed for a system for use in either the home of a user or patient or the office of a health care provider that can provide an HbA1c assessment quickly and accurately. Typically, a system designed for a person, such as a diabetic, who is not medically trained, to assay a blood sample for HbA1c includes a test strip and a test meter. The test strip and test meter is generally used to determine the amount of irreversibly glycated hemoglobin, HbA1c, relative to the amount of total hemoglobin, Hb, present in a sample of blood. Existing assay systems that can be used to determine an HbA1c value or percentage include the DCA 2000 analyzer of Bayer Diagnostics of Tarrytown, N.Y., the Glycosal test of Provalis Diagnostics Limited of Flintshire, in the United Kingdom, and the A1cNow monitor commercially available from Metrika, Inc. of Sunnyvale, Calif., by way of example.

In recent years, research efforts have focused on creating assays that are both highly accurate and fast. However, existing HbA1c assays typically require a series of steps involving pre-treatment of a blood sample, such as the dilution of a blood sample and/or the lysing of the blood cells in the blood sample, and the subsequent treatment of the sample to separate its various components. In some of these existing HbA1c assays, one or more of the pre-treatment steps must be carried out by the user before he or she can use the test device to assay the blood sample. For example, the above-referenced A1cNow monitor, which is based on technology described in U.S. Pat. No. 5,837,546 of Allen et al., entitled "Electronic Assay Device and Method," which is incorporated herein in its entirety by this reference, is said to provide an HbA1c test result in eight minutes using a relatively small sample of blood. However, a user of the A1cNow monitor must dilute the blood sample prior to testing the diluted sample using the A1cNow monitor. Further by way of example, it is believed that the above-mentioned Glycosal test requires lysing of the blood sample prior to testing the lysed sample using the Glycosal test. Systems and methods that require such pre-treatment of a sample by a user are generally not convenient or easy for the user and are subject to user error. These systems and methods are thus not ideal for users in self-test situations. Likewise, as these systems and methods require pre-treatment steps on the part of a physician in physician-test situations, they are not particularly convenient or ideal for a physician to use in an office setting. Further development of blood glucose assay devices and systems, and methods of using same, is desirable.

SUMMARY OF THE INVENTION

The present invention provides devices, systems, and methods that are convenient means for a user, such as a patient or a health care practioner, to obtain a reading corresponding to an amount of an analytes or multiple analytes in a sample from a physiological source. Advantageously, such devices, systems and methods can be used upon the user obtaining a sample of blood, for example, using conventional means such as a lancing device, applying the sample to a test strip, and inserting the test strip in the test meter, whereupon the meter provides a result in the manner of minutes, such as from about two to about six minutes. That is, typically, the user need not precondition or manipulate the sample in any complicated or error-prone manner prior to using the test device, need not further condition or process the sample on the test strip during testing with the test device, and need not wait long for a test result.

According to one aspect of the invention, a system for optically or spectrophotometrically determining total hemoglobin and glycated hemoglobin in a blood sample, is provided. The system includes a meter device that comprises a user interface, including various user controls and a result display or output, a test strip receiving area, a movable door for covering and uncovering a test strip received in the receiving area, a test strip receiving area, an optical subsystem for optically testing the sample along a portion or portions of the test strip, and an electronic subsystem for processing the results of the optical test and communicating an ultimate test result to the result display or output.

The system also includes a test strip that comprises a sample application zone, a hemolysis zone, a glycated hemoglobin capture zone, a non-glycated hemoglobin zone, arranged along a wicking membrane of the test strip. The hemolysis zone and the glycated hemoglobin capture zone are produced by striping various portions of the wicking membrane with a hemolysis agent, such as a detergent, and a hemoglobin capture reagent, such as an antibody or a chemical reagent having boron ligands, respectively. The test strip further comprises an area for application of an eluting agent to the test strip, either manually or via a holding device that releases an eluting agent upon the occurrence of a release condition. The eluting agent serves to move the hemoglobin that is liberated upon hemolysis down the wicking membrane toward the glycated hemoglobin capture zone and the non-glycated hemoglobin zone.

The system is designed such that the test strip zones of interest for measurement purposes are aligned with the optical subsystem of the meter device. That is, a zone of interest or multiple zones of interest are in optical communication with a lighting device, such as a light-emitting diode (LED), or multiple lighting devices, such that they receive light from such a device or devices. The LEDs provide light of predetermined wavelength according to the analyte of interest, which light is absorbed, transmitted, and reflected variously by the analytes in the sample in the zone or zones of interest. A light detector of the optical system is situated to detect the reflected light, for example, whereupon it provides an electrical signal corresponding to an amount of an analyte or amounts of several analytes. The electrical signal is transmitted to the electronic subsystem of the meter device for processing to obtain a result or results of interest to the user, such as a percentage of HbA1c in a blood sample. The electronic subsystem thus includes components such as a microprocessor and a memory for carrying out various calibrations and calculations to obtain such results and communicate them to the display of the meter device or to other output means.

Preferably, both the meter device and the test strips are of relatively simple and low-cost construction. The test strip is designed to accept a sample, to be inserted into the optical meter for a spectrophotometric determination of an analyte or analytes in the sample, and preferably, to be removed from the optical meter and discarded after such a determination. The optical meter is preferably designed for use with any number of these single-use test strips. The system is preferably designed to have a small footprint, such that a user can conveniently use it in the palm of the hand.

The system and the devices and methods associated therewith are conducive to home use by a user who may not be medically trained and to office use by a health care practitioner. The system, devices and methods of the invention are particularly useful in the monitoring and treatment of diabetic patients.

BRIEF DESCRIPTION OF THE DRAWINGS

A detailed description of various aspects, features and embodiments of the present invention is provided herein with reference to the accompanying drawings, which are briefly described below. The drawings are illustrative and are not necessarily drawn to scale. The drawings illustrate various aspects or features of the present invention and may illustrate one or more embodiment(s) of the present invention in whole or in part. A reference numeral or symbol that is used in one drawing to refer to a particular element or feature may be used in another drawing to refer to a like element or feature.

FIG. 1A is a schematic illustration of a meter device according to one or more aspect(s) of the present invention, from an elevated view of a top, a width and a length of the device.

FIG. 1B is a schematic illustration of a door of a meter device according to one or more aspect(s) of the present invention, from an elevated view of an underside of the door.

FIG. 1C is a schematic illustration of a door of a meter device according to one or more aspect(s) of the present invention, from an elevated view of an underside of the door.

FIGS. 1A, 1B and 1C are sometimes collectively referred to as "FIG. 1" herein by way of simplicity or convenience.

FIG. 2 is a schematic illustration of a meter device according to one or more aspect(s) of the present invention, with a portion of the meter device removed for illustration purposes, from an elevated view of a top, a width and a length of the device. FIG. 2 further includes a schematic illustration of a test strip in relation to the meter device.

FIG. 3 is a schematic illustration of a meter device according to one or more aspect(s) of the present invention, from an elevated view of a top, a width and a length of the device. FIG. 3 further includes a schematic illustration of a test strip in relation to the meter device.

FIG. 4A is a schematic illustration of a test strip according to one or more aspect(s) of the present invention, from an elevated view of a top, a width and a length of the test strip.

FIG. 4B is a schematic illustration of a test strip according to one or more aspect(s) of the present invention, from a side view of a cross-section taken along a length of the test strip. FIG. 4B further includes a schematic illustration of a sample to be tested and light devices of a meter device (not shown), from a corresponding cross-sectional side view.

FIGS. 4A and 4B are sometimes collectively referred to as "FIG. 4" herein by way of simplicity or convenience.

FIG. 5A is a schematic illustration of a test strip according to one or more aspect(s) of the present invention, from an elevated view of a top, a width and a length of the test strip.

FIG. 5B is a schematic illustration of a test strip according to according to one or more aspect(s) of the present invention, from a side view of a cross-section taken along a length of the test strip. FIG. 5B further includes a schematic illustration of a sample to be tested and a light device of a meter device (not shown), from a corresponding cross-sectional side view.

FIGS. 5A and 5B are sometimes collectively referred to as "FIG. 5" herein by way of simplicity or convenience.

FIG. 6 is a schematic illustration of a test strip according to one or more aspect(s) of the present invention, from a side view of a cross-section taken along a width of the test strip. FIG. 6 further includes a schematic illustration of a sample to be tested and light devices of a meter device (not shown), from a corresponding cross-sectional side view.

FIG. 7 is a schematic illustration of a test strip according to according to one or more aspect(s) of the present invention, from a side view of a cross-section taken along a length of the test strip. FIG. 7 further includes a schematic illustration of a sample to be tested and a light device of a meter device (not shown), from a corresponding cross-sectional side view.

FIG. 8 is a schematic illustration, partially in the form of a block diagram, a portion of a test strip, an optical system of a meter device, and an electronic system of a meter device, according to one or more aspect(s) of the present invention.

DETAILED DESCRIPTION

This invention is generally directed to a strip and meter system for determining the presence of, and the amount of, an analyte or various analytes in a sample, such as a sample from a physiological source. The invention is also directed to various devices and methods associated with such a system. Merely by way of illustration, the invention is particularly described in relation to systems, and associated devices and methods, for determining glycated hemoglobin in a blood sample, although it will be understood that the invention is not so limited.

The invention is now described in relation to a strip and meter system for a spectrophotometric determination of glycated hemoglobin, or HbA1c, in a blood sample, such as a sample of venous or capillary whole blood. The strip and meter system is preferably designed such that diabetics and health care providers will find it easy to use. In particular, the strip and meter system is preferably designed such that blood preparation is kept to a minimum. That is, according to various aspects of the present invention, the only blood preparation that is called for on the part of the user is the obtaining of a drop of blood and the application of that drop to a test strip. As such, the system is well suited to home use by a user who may or may not be medically trained, or by a health care provider during a patient's visit to the office of the health care provider.

In this invention, the HbA1c meter is the instrument component of the HbA1c monitoring system. The meter is preferably a handheld device that measures the electrical output from an optical test of an HbA1c test strip that is the site of a reaction involving HbA1c from a whole blood sample. The electrical output is generated by an optical system of a type suitable for blood glucose testing, as further described herein. This electrical output is converted into a percentage of HbA1c, using calibration algorithms and simple arithmetic calculations that are built into the meter, and this percentage is displayed to the user.

The HbA1c meter is designed as an integration of analog and digital circuitry, electronic, optical and mechanical components, which are preferably off-the-shelf, commercially available components, and a unique mechanical design that includes a door or cover that is positioned over a strip-receiving portion of the meter. The meter generally comprises a user interface and a measurement subsystem for overall control of meter functions, and an internal microprocessor for processing, controlling and communicating various data associated with the meter.

The structure of the meter 100 according to various aspects of the invention is schematically illustrated in FIGS. 1-3. The meter 100 comprises a door 10, which is in shown in a closed configuration in FIG. 1A. In operation, the door 10 is placed in an open configuration to permit the insertion of test strip 200. By way of illustration, the door 10 is not shown in FIG. 2, such that the presence of the test strip 200 relative to the meter 100 can be seen. Further by way of illustration, door 10 is shown in a closed configuration in FIG. 3, such that it covers at least a portion of the test strip 200 that is inserted in the meter 100. Preferably, the door itself or a door latch (not shown) presses down on the test strip to secure it against a test strip platform 60 (FIG. 2) of the meter device 100.

The door 10 may be attached to the meter 100 via a hinge 20 to facilitate the opening and closing of the door, as shown in FIG. 1A. While the hinge 20 is shown at an upper position relative to the door 10 in FIG. 1A, it may just as easily be positioned elsewhere, such as a side position relative to the door 10, as can be seen in the underside view of the door 10 shown in FIG. 1B. Still other door-attachment mechanisms, such as a track system 70, comprising any combination of complementary raised tracks and track grooves, along which the door can slide, for example, as can be seen in the raised tracks 72 or track grooves 74 schematically shown on the underside view of door 10 shown in FIG. 1C, are contemplated, where complementary track grooves (not shown) or raised tracks (not shown), or any combination thereof, would appear on the test strip platform 60 of the meter 100.

The meter 100 may comprise a button 30 for turning the meter on, or for turning the meter on and off. Alternatively, the meter 100 can be turned on automatically upon insertion of the test strip 200 into the meter and turned off automatically upon removal of the test strip from the meter. In the latter, preferred case, a portion of the test strip 200 that is inserted into the meter 100, such as an end portion 228 of the test strip 200, for example, comprises a conductive material 226, as schematically illustrated in FIG. 4A, which may take the form of a coating, for example. The conductive material 226 serves to close an opened switch circuit in the meter 100 when the test strip 200 is inserted in the meter and thereby turn the meter on, and to open the closed switch circuit in the meter when the test strip is removed from the meter and thereby turn the meter off. Such switch opening and closing via a conductive material on an object is generally known, and any suitable conductive material can be used.

The meter 100 may include a display 50, such as a liquid crystal display, for example, to display a result to a user. Other means of communicating a result from the meter may be used, such as a communication port 680, by which a result may be communicated to a peripheral device, for example.

The meter 100, and its various components, may be configured in any of a number of forms, shapes and structures other than the particular forms, shapes and structures shown in FIGS. 1-3. Accordingly, a test strip 200 for use in connection with the meter 100 may take on any of a variety of forms, shapes and structures that are conducive to use in relation to the meter. Various suitable test strips 200 are schematically shown in FIGS. 4-7 and further described herein.

Typically, in order to use the meter 100, the user obtains a small blood drop (about less than or equal to about 10 microliters, such as about 2 or about 3 microliters to about 5 microliters, for example), such as the hanging blood drop 700 schematically shown in FIGS. 4B, 5B, 6 and 7. The blood drop can be obtained from venous or capillary whole blood, for example. Naturally, any other whole blood, such as arterial whole blood could be used in connection with the meter, although its procurement may be more complicated, such that it is not preferred. The user typically obtains a blood drop or sample 700 using a lancing device on a finger, for example, or using a needle and a syringe on a vein, for example, although any suitable means or methods for obtaining a blood sample can be used. The user then applies the blood sample 700 to an application zone, well or pad 216 on the test strip 200, as shown in FIGS. 4-7. Such application typically involves simply letting the drop 700 fall onto the application well or zone 216, although any suitable means or methods for applying the sample to the application zone can be used. Such application can take place before or after the test strip 200 is inserted in the meter 100, the latter being preferred.

Once the blood sample 700 has been applied to the test strip and the test strip has been positioned in the meter 100, the sample penetrates the strip structure and cell lysing occurs, as further described herein. Typically, such penetration and lysing proceeds very quickly, or it may take a short time, such as from about 10 seconds or about 15 seconds to about 30 seconds, or perhaps up to about 1 minute, merely by way of example. It is not necessary that the entire sample be lysed, for example, lysing of more or less than 50% or about 50% of the cells in the sample may be sufficient. During sample penetration and cell lysing, the door 10 of the meter 100 may be left open, as it is in some embodiments. Afterwards, the door 10 is closed and testing of the sample proceeds, as further described herein. The testing of the blood sample results in a test result, obtained via calibration and/or calculation, such as calibration involving the use of a calibration code or calibration codes, as schematically represented by calibration code selection button 40 on meter 100, and calculations, such as simple arithmetic or ratiometric manipulations of numbers. Typically, a test result is obtained in a period of from about 2 minutes or about 3 minutes to about 5 minutes after the door 10 is closed.

The meter 100 of the invention includes a specially designed door 10. When the door 10 is closed, it functions to block extraneous light from entering the meter 100, such that interference with optical measurements is reduced or eliminated. Thus, preferably, the door 10 is made from a material of sufficient opacity to block such extraneous light and is of a construction sufficient to block such extraneous light. By way of example, the door 10 may be composed of opaque material that is lightly colored (such as white, for example) to more darkly colored (such as blue, purple or black, for example), relatively dark-colored materials being preferred. Further by way of example, the door 10 may be of a construction or configuration relative to the meter 100 sufficient to render it leak-proof in terms of light exterior to the meter 100. Preferably, the door 10 is configured relative to the meter 100 in a manner such that when the door 10 is closed, it also functions to hold a test strip 200 down against the test strip platform 60 of the meter.

In some embodiments, as further described herein, the door 10 is configured and constructed in a manner such that when it is closed, it also functions to simultaneously depress and cause the rupture of a pouch or blister 230 that is integrated with a test strip 200. By way of example, the door 10 may have a structure 80 comprising a breaking means, such as a sharp or roughened point, blade, or surface, that is sufficient to cause a break in the integrity of a pouch or blister 230 of a test strip 200, when the door is closed over such a test strip that has been properly positioned in the meter. A door 10 having such a structure 80 on its underside is shown by way of illustration in FIGS. 1B and 1C. The pouch or blister 230 contains an eluting solvent, such as a buffer solution, that is used in the test process, as further described herein. Various embodiments of the invention, which may incorporate the solvent-containing pouch or blister 230, are further described below.

According to an embodiment of the invention, the meter 100 generally has no moving parts other than, for example, an on or on/off button 30, a calibration code selection button 40, a door 10, and a device for moving the door, such as a door hinge 20 or a track system 230. While the on/off button 30 and the code selection button 40 are shown as two separate buttons in FIGS. 1-3, they may be integrated into a single, multifunctional button (not shown). Further, while buttons are described, other means, such as keystrokes on an alphanumeric keyboard (preferably, of small dimensions), for example, could be used for on/off and code selection functions. The optical meter 100 further comprises an optical system 550 having a light detector and a light emitting diode (LED) or multiple LEDs, such as two LEDs, appropriately positioned within the meter housing to determine amounts of analytes, such as the total hemoglobin and the glycated hemoglobin in the sample, as further described in relation to FIG. 8. The optical meter 100 also comprises an electronic system 650 suitable for processing one or more electrical signal(s) from the light detector to provide, via calibration and/or calculation, a quantitative value corresponding to the amount of glycated hemoglobin in the blood sample, such as a % HbA1c, also as further described in relation to FIG. 8. As described above, the meter 100 is designed for testing a blood sample 700 that is applied to a test strip 200, which is now described.

A test strip 200 for use in an embodiment of the invention is schematically shown in FIGS. 4A and 4B. As shown in these Figures, the test strip 200 extends from one end, where a test strip handle 212 is located, to another end 228. Generally, the one end defines an upstream end and the other end 228 defines a downstream end, with a position, portion, or area between the two ends being defined as upstream or downstream relative to another position, portion, or area on the test strip 200. A similar convention is generally used in connection with the test strips 200 shown in FIGS. 5 and 7.

The test strip 200 generally includes a substrate 210, a test strip handle 212, a reservoir or pad 214, and a sample application zone 216. The test strip handle 212 may be part of the substrate 210, such as a solid, flexible substrate, for example, that supports at least the reservoir or pad 214 and the sample zone 216, or it may be supported by the substrate 210. The substrate 210 is of a construction sufficient for insertion into the meter 100, comprising a solid, flexible support, for example. It should be noted that a substrate 210 may not be necessary for the test strip 200, for example, where the test strip is comprised of elements, such as the wicking membrane further described herein, that are of a construction sufficient for self-support. As previously described, the test strip 200 may comprise a conductive material 226 on a portion thereof, such as an end portion 228, for example, as shown in FIG. 4A, that can be used to turn on the meter 100 when the test strip is inserted in the meter.

Below the sample application well or zone 216 of the text strip 200 is a wicking membrane 218 that is striped with various reagents to create various reagent, capture and/or eluate zones, such as zones 220, 222 and 224. The wicking membrane 218 typically starts at the sample application zone 216 and extends through the zones 220, 222, and 224, and may extend therebeyond, such as to the end portion of the strip 228. The wicking membrane 218 preferably has sufficient absorbent properties such that it is sufficient to absorb all of the various fluids associated with the assay, such as the blood sample 700 and the eluting agent further described herein, such that substantially no fluid flows from the test strip into the meter 100. By way of example, a suitable wicking membrane may be comprised of a material sufficient for wicking or capillary action material, such as a nylon or a nitrocellulose material, of a porous material, such as a polyethylene sheet material, or of any combination of such materials. The wicking membrane 218 is the basis for a migration assay contemplated herein, wherein a sample 700 is wicked through the wicking membrane and various sample components undergo various reactions or elute through various portions of the wicking membrane, and these various portions are then tested for indications corresponding to amounts of the various sample components.

As mentioned above, the wicking agent 218 is prepared such that it has various zones. By way of example, a hemolysis reagent zone 220 of the wicking membrane 218 may be positioned immediately below the opening of this sample application zone 216. The hemolysis reagent zone 220 comprises a hemolysis reagent that is striped, such as absorbed, confined, or immobilized, on the wicking membrane 218 of the test strip 200. Typically, a small amount of hemolysis reagent, such as about 1 to about 2 or about 3 microliters, for example, is sufficient for striping the wicking membrane such that the hemolysis reagent zone 220 is sufficiently confined on the test strip 200. Any reagent or combination of reagents suitable for hemolysis, and the consequent liberation of hemoglobin, can be used. By way of example, an ionic detergent, such as sodium dodecyl sulfate (SDS), a non-ionic detergent, such as a octylphenol ethylene oxide condensate or octoxynol-9 or t-octylphenoxypolyethoxy-ethanol, sold under the name, Triton X-100, and commercially available from Sigma Chemical or Sigma-Aldrich Co., or a hypotonic solution, may be used as a hemolysis reagent.

The user can apply an eluting agent, such as a solvent, a buffer solution, or any combination thereof, to pad 214, such as a soft absorbent pad, located upstream of the sample application zone 216 and hemolysis zone 220 on the test strip 200. This pad 214 may be a soft, absorbent pad for storing or holding the eluting agent temporarily, prior to use, and releasing the eluting agent at the time of use upon a release condition, such as the application of pressure to the pad, such as in a sponge-like manner, or the application of eluting agent beyond the absorbent capacity of the pad, for example. Alternatively, as described herein in relation to FIG. 5B, the eluting agent can be carried in a pouch or blister 230 affixed a portion of the test strip 200 that is located upstream of the sample application zone 216 and hemolysis zone 220 on the test strip 200. The pouch or blister 230 can be made to hold the eluting agent therein or to hold the eluting agent by way of absorption on a soft absorbent pad 240 located therein, until a release condition occurs, such as a break in the integrity of the pouch or the application of pressure to the pouch, such that the eluting agent is released from the pouch 230 or the soft absorbent pad 240.

Once a sample has been applied and permitted to penetrate through the hemolysis zone 220, the elution agent is applied to pad 214, or released from pouch 230 or pad 240, and the buffer elutes the hemolysed sample, freeing the liberated hemoglobin from the hemolysis zone 220. Any buffer or combination of buffers suitable for elution of a lysed blood sample, such as a phosphate buffered saline solution, may be used. Merely by way of example, a phosphate buffered saline solution of from about 0.01 molar to 0.02 molar, may be used, although other suitable concentrations are contemplated.

The wicking membrane 218 is also striped, using suitable chemistry, to create a glycated hemoglogin capture zone 222 downstream relative to the hemolysis zone 220. By way of example, any chemical reagent comprising at least one boron ligand, such as phenyl boronate or other boron affinity chemistry used in the above-referenced Glycosal test, or such as m-aminophenylboronic acid, such as that of a gel that is immobilized on cross-linked, beaded agarose as disclosed in U.S. Patent Application Publication No. 2002/0172992 A1, which is incorporated herein in its entirety by this reference, any antibody, such as anti-HbA1c antibody available from a number of sources, any immunoassay reagent, any chemical reageng comprising at least one binding ligand, such a boronic acid involving boron binding ligands, and the like, and any combination thereof, that is suitable for the binding of glycated hemoglobin to the capture zone 222, such as via covalent bonds, for example, or the capture of glycated hemoglobin in capture zone 222, may be used.

As the buffer elutes components of the sample 700 downstream along the test strip 200, glycated hemoglobin components are captured at the glycated hemoglobin capture zone 222, and other hemoglobin components continue on to eluate zone 224 of the wicking membrane 218. While it is not necessary to capture the non-glycated hemoglobin, preferably, the eluate zone 224 has been treated, for example, using one or more chemical reagents, to create a non-glycated hemoglobin capture zone 224, where non-glycated hemoglobin is captured. Any chemical reagent that is suitable for this purpose, such as any of a specific antibody, a glycoprotein, such as haptoglobin, for example, any chemical reagent comprising a suitable binding ligand, and the like, and any combination thereof, can be used.

Any of the zones 220, 222 and 224 may be of interest for measurement purposes. By way of example, zone 220 is typically of interest for the measurement of total hemoglobin in the sample, and capture zone 222 is typically of interest for the measurement of glycated hemoglobin in the sample. Eluate zone 224 may also be of interest for the measurement of non-glycated hemoglobin in the sample. An LED is positioned beneath such a zone of interest, or multiple LEDs are positioned beneath such zones of interest, respectively, for measurement purposes. Such an LED is used to obtain an optical signal that relates to the amount of the analyte of interest. The test strip platform 60 of the meter device 100 has one or more opening(s) or window(s) (not shown) corresponding to one or more zones(s) of interest, respectively, such that there is a clear optical path between the LED(s) and the zone(s) of interest. Light striking the zone(s) of interest is absorbed, transmitted or reflected by the sample 700 at the zone(s) of interest, such that a portion of the light is transmitted or reflected toward a light detector, as further described herein. The light, or optical signal, is received by the light detector, whereupon it is converted to an electrical signal that is sent to a microprocessor, preferably, a microprocessor internal to the meter 100, for the processing of the measurement to obtain a result of interest to the user, such as a ratiometric relation (for example, a simple percentage relation) of the amount of glycated hemoglobin (i.e., lysed hemoglobin that is glycated) relative to the amount of total hemoglobin (i.e., total lysed hemoglobin) in the sample.

Thus, according to an embodiment of the invention, zones 220 and 222 may be located at different positions along the length of the test strip 200, as described above. In such an embodiment, one LED 400 may be placed beneath zone 220 and another LED 410 may be placed beneath capture zone 222, as shown in FIG. 4B. Other LED placements are contemplated. By way of example, an LED could be placed above the zone of interest, provided there is a free optical path between the LED and the zone of interest (i.e., the door 10 may need to be located beneath the test strip). Further by way of example, the LEDs could be placed adjacent a side of the zone of interest, provided there is sufficient light-interaction in the zone of interest for a meaningful reading (i.e., the test strip may need to be thicker such that the target side is larger). Still further, an LED (not shown) could be placed in operable relation to zone 224.

The LED 400 may emit light at any wavelength suitable for obtaining an optical signal relating to the total amount of hemoglobin in the sample. Typically, such a signal is obtained upon the application of the sample 700 to the sample application zone 216 and the hemolysis of the sample in the hemolysis layer 220. The LED 410 may emit light at any wavelength suitable for obtaining an optical signal relating to the amount of glycated hemoglobin in the sample. Typically, such a signal is obtained upon the application of the elution agent to the sample, as previously described, such that glycated hemoglogin becomes bound to or captured in capture zone 222.

The LED 400 and the LED 410 may emit light of the same wavelength or of similar wavelengths, or may emit light of different wavelengths. It may be desirable to use LEDs that emit light at different wavelengths to reduce or eliminate the possibility of interference or resolution problems. Further, in the selection of an LED that emits light of an appropriate wavelength, it should be noted that hemoglobin exhibits a strong reflectance peak at about 415 nm. Merely by way of example, the LED 400 may emit light in the near infrared region, such as light of a wavelength of from about 930 to about 950 nm, such as about 940 nm. Further by way of example, the LED 410 may emit light in the visible region, such as light of a wavelength of from about 400 nm to about 600 nm or about 700 nm, such as from about 540 to about 590 nm, or such as about 410 nm, about 550 nm, about 560 nm, or about 575 nm.

According to another, more preferred embodiment of the invention, the meter 100 is much like that described above, while the test strip 200 is differs in some ways. As described above and shown in FIG. 5A, the test strip 200 comprises a sample application zone 216 for manual application of a sample and an elution pad 214 for manual application of an eluting agent, such as an eluting solvent or buffer. Alternatively, a pouch or blister 230 containing an eluting agent can be positioned in this area of the strip, as shown in FIG. 5B. Regardless of which of these alternatives is selected, a hemolysis layer/zone 220 is positioned below the sample application zone 216 and a glycated hemoglogin capture zone 222 of a wicking membrane 218 is positioned below the hemolysis layer/zone 220, as shown in FIG. 6. Thus, in addition to the general convention regarding upstream and downstream positions along a length of the test strip 200, as previously described, here is also a general convention by which the sample application zone 216 is upstream relative to the hemolysis layer/zone 220, which is upstream of the glycated hemoglobin capture zone 222. Alternatively, the hemolysis layer/zone 220 and the glycated hemoglobin capture zone 222 can be integrated to form an integrated reagent zone 300, as further described in relation to FIG. 7. As previously described, the wicking membrane 218 may further comprise a non-glycated hemoglobin zone 224 positioned downstream from the glycated hemoglobin capture zone 222, as shown in FIGS. 5 and 6, or downstream from the integrated reagent zone 300, as shown in FIG. 7.

Accordingly, in the meter 100, one LED, such as the LED 500 shown in FIG. 5B, or multiple LEDs, such as the LED 500 and the LED 510 shown in FIG. 6, may be positioned beneath the above-described zones 220 and 222, such that signals relating to the total amount of hemoglobin in the sample and the amount of glycated hemoglobin in the sample may be obtained for further processing to obtain a result of interest to the user, such as a ratiometric relation (for example, a percentage relation) of the amount of glycated hemoglobin relative to the total amount of hemoglobin in the sample. For the meter 100 shown in FIG. 7, one LED 500 may be positioned beneath the above-described integrated reagent zone 300 and used to obtain such signals for such further processing. Further, as mentioned previously, an LED (not shown) may be positioned in operable relation to eluate zone 224 to obtain a signal relating to the amount of non-glycated hemoglobin in the sample.

When the sample 700 is added to the sample application zone 216 of the test strip 200, it undergoes hemolysis via a hemolysis reagent in the hemolysis layer 220, as previously described. At this time, an optical signal is obtained via an LED, such as the LED 500 shown in FIG. 5B and FIG. 7, or either of the LED 500 and the LED 510 shown in FIG. 6, positioned below the hemolysis layer 220 (FIGS. 5 and 6) or the integrated zone 300 (FIG. 7) of the test strip 200 and processed to obtain an amount of hemoglobin in the sample, or a total percentage of hemoglobin in the sample.

Upon hemolysis of the sample, the glycated hemoglobin in the sample becomes bound to the glycated hemoglobin capture zone 222 (FIGS. 5 and 6) or integrated zone 300 (FIG. 7). As previously described, the sample is the eluted such that the non-glycated hemoglobin of the sample is eluted away from the hemoglobin capture zone 222 or integrated zone 300 toward the non-glycated hemoglobin zone 224, via the wicking action or capillary action or draining pores of the wicking membrane 218.

Thus, following hemolysis, an elution agent is added to the sample to elute it, as previously described, for example, manually via an eluant-loaded elution pad 214, as shown in FIG. 5A, or via a eluant-loaded blister pack 230, as shown in FIG. 5B. In the latter case, the blister 230 may be manually ruptured, or more preferably, ruptured upon closing the meter door 10, for example, via a structure 80 having a sharp or rough feature, as shown in FIGS. 1B and 1C, on a portion of the door 10 that contacts the blister 230 as the door is closed. While a rupture is sometimes referred to herein, any sufficient compromise to, or break in, the integrity of the blister 230, such that the elution agent is liberated therefrom, is sufficient. The blister pack 230 containing the eluting agent may be designed to include an absorbent pad 240, as shown in FIG. 5B, such that when the blister is ruptured and the solvent is released therefrom, the wicking or capillary action of the wicking membrane 218, which is preferably disposed adjacent the absorbent pad 240, will cause the eluting agent to travel downstream of the absorbent pad along the wicking membrane.

When the elution agent is applied to the sample, via manual or blister-pack means, the glycated hemoglobin and the non-glycated hemoglobin undergo separation, for example, chromatographic separation, such that the non-glycated hemoglobin is eluted in a direction away from the glycated hemoglobin capture zone 222 or integrated reagent zone 300 toward non-glycated hemoglobin zone 224. At this time, an optical signal is obtained via an LED, such as the LED 500 shown in FIGS. 5B and 7, or either of the LED 500 and the LED 510 shown in FIG. 6, positioned below the glycated hemoglobin capture zone 222 (FIGS. 5 and 6) or integrated zone 300 (FIG. 7) of the test strip 200, which LED may or may not be the same LED used to obtain the optical signal relating to the total hemoglobin in the sample. The optical signal is then processed to obtain an amount of glycated hemoglobin in the sample, or further processed to obtain a result of interest to the user, such as a ratiometric relation (for example, a percentage relation) of the amount of glycated hemoglobin relative to the total amount of hemoglobin in the sample.

When one LED 500 is used, as schematically shown in FIGS. 5B and 7, it is used to obtain the two optical signals described above at the different times described above. In such a case, the LED 500 may emit light of the same wavelength or of similar wavelengths, or may emit light of different wavelengths, at the different times it is employed. When two LEDs are used, such as the LED 500 and the LED 510 as schematically shown in FIG. 6, one LED is used to obtain the first optical signal described above at the time described above, and the other LED is used to obtain the second optical signal described above at the other time described above. The LED 500 and the LED 510 may emit light of the same wavelength or of similar wavelengths, or may emit light of different wavelengths. Merely by way of example, any of the LED 500 and the LED 510 may emit light in the near infrared region, as described above, or in the visible region, as described above.

Typically, test strips 200 for use in connection with the meter device 100 are manufactured in lots. These lots are typically provided with calibration codes. Such calibration codes can be entered into the meter device via the calibration code selection button 40 of the meter device 100 and employed as described herein or in a known manner for calibration purposes. The test strips 200 typically have a shelf life of about 18 months when properly stored, such as at a temperature of about 30° C. The test strips 200 may be treated with a shelf-life preservative, provided same would not interfere with the performance of the test strips in the assay. The test strips can be used over a range of temperatures, such as from about 4.4° C. to about 40° C.

The test strip 200 can take any of a wide variety of forms, such as one of its preferred forms shown in FIG. 7, for example. By way of example, a test strip 200 may comprise a handle portion 212, which supports only an upper portion 250 of the test strip, such as a portion upstream relative to the sample application zone 216. The test strip 200 may be supported in other of its portions, such as an intermediate portion 260 located downstream relative to the sample application zone 216, and/or a lower portion 270 located downstream relative to the intermediate portion, as shown in FIG. 7. Supportive substrates may vary in construction and/or form, such as from thick (see supportive structures 212 and 280 in FIG. 7) to thin (see supportive structure 290 of FIG. 7) relative to the supported structures, from rigid to flexible relative to the supported structures, and the like, being sufficient to support a particular portion of the test strip 200. It is contemplated that a test strip 200 comprised of a self-supporting structure, such as a wicking membrane 218 of sufficient rigidity, while preferably of some flexibility, for example, may be constructed, such that one or more separate supportive substrate(s) are unnecessary.

In the test strip 200 shown in FIG. 7, the eluant reservoir or pad 214, may be partially or wholly housed in a flexible casing 310. By way of example, a plastic-lined foil pouch, such as a polyethylene-lined foil pouch, may be used for the flexible casing 310. This flexible casing 310 may be used in any location where it may be punctured or depressed to release an eluting agent, as previously described, such as on a top and/or a side portion of the reservoir or pad 214/230, merely by way of example. As previously mentioned, the hemolysis reagent zone 220 (as shown in FIGS. 4-6) and the glycated hemoglobin capture zone 222 (as shown in FIGS. 4-6) located at or beneath the sample application zone 216, where the sample drop 700 is applied to the test strip 200, may be in the form of an integrated zone 300, as schematically illustrated in FIG. 7. This integrated zone 300 is treated with a hemolysis reagent and a glycated hemoglobin capture reagent, such that it performs the previously described functions of the hemolysis reagent zone 220 and the glycated hemoglobin capture zone 222. Remaining portions of the wicking membrane 218 that are located downstream relative to the integrated zone 300, such as a non-glycated capture zone 224, may be partially or wholly housed by a plastic laminate 320, for example, on a top and/or a side portion of the wicking membrane 218, and by a flexible plastic substrate 330 on a bottom portion of the wicking membrane.

As previously described, at least one LED 500 of a meter device 100 may be disposed relative to, such as beneath, the integrated zone 300, such that the meter device can detect a total amount of hemoglobin in the sample and an amount of glycated hemoglobin in the sample, and display a result of interest to the user, such as an HbA1c percentage, for example, on a display 50 (as shown in FIGS. 1-3) of the meter device 100.

A schematic illustration of an optical system 550 of a meter device 100, such as that of FIGS. 1-3, is shown in FIG. 8. Though not shown in FIG. 8, the optical system 550 is housed in the meter device 100, preferably in a manner that allows as little as possible or no extraneous light (i.e., light not associated with light emitted by the LED(s) employed and light reflected by the analyte(s) of the sample 700 in the zone of interest) to enter the meter device 100. As previously described, one LED or several LEDs may be variously employed in the optical system of the meter device 100 and may be arranged accordingly. By way of example, the LED or LEDs may be spatially arranged to correspond with the location of the zone(s) of interest on the test strip 200, and directionally arranged to target the zone(s) of interest. A light detector of the optical system may be arranged accordingly, in a similar manner, to receive light that is reflected by the sample 700.

Merely by way of example, the two LEDs 500 and 510 depicted in FIG. 8 are arranged, such as spatially and directionally arranged, within a meter device 100 such that light emitted therefrom is directed toward a zone of interest in the test strip 200, such as integrated zone 300 of the test strip 200 of FIG. 7, or hemolysis zone 220 or glycated hemoglobin capture zone 222 of the test strip 200 of FIG. 6, for example. While the two LEDs 500 and 510 are depicted as being located underneath the test strip 200 in FIG. 8, other configurations are possible. When light from LED 500 or LED 510 reaches the zone 300/220/222 of interest, it may be scattered in a manner indicated by arrows 520 in a direction more or less away from an optical detector 540, and/or in a manner indicated by arrows 530 in a direction more or less toward the optical detector 540 of the optical system 550. The nature of this scatter will depend on the nature of the sample in the zone 300/220/222 of interest, such as its properties of absorbance, transmission, or reflectivity in relation to light of various wavelengths.

When light is scattered in the manner just described, the optical detector 540 receives at least a portion of the scattered light, such as at least a portion of the light reflected more or less toward it, as indicated by arrows 530. The amount of light picked up by the optical detector 540 will depend on factors such as the detection limits or tolerances of the particular detector used. Thus, the optical detector 540 should be selected or adjusted such that meaningful readings are obtained. When light is received by the optical detector 540, it produces an electrical signal 560 (schematically represented by a ~ symbol in FIG. 8) that corresponds to the amount of light received. As mentioned previously, this electrical signal 560 may be processed to provide a meaningful result to a user, such as a percentage of HbA1c in a blood sample 700 that may be displayed to the user via display 50 of the meter device 100, as shown in FIGS. 1-3.

A schematic illustration of an electronic system 650 of a meter device 100, such as that of FIGS. 1-3, is also shown in FIG. 8. Though not shown in FIG. 8, the optical system 550 is housed in the meter device 100. The electronic system 650 generally comprises an on/off switch 600, a microprocessor 610, a memory device 620, and a display 630. The on/off switch 600 may be in operable communication with an on or on/off button of the meter device 100, such as on or on/off button 30 shown in FIGS. 1-3, or in operable communication with a conductive portion 226 of a test strip 200 shown in FIG. 4A, as previously described.

By way of example, when the meter device 100 is in an "off" condition and the button 50 is activated, in any suitable manner, such as by depression or by changing its position (i.e., like a light switch), for example, the switch 600 is activated such that the meter device 100 is placed in an "on" condition; and when the meter device is in an "on" condition and the button 50 is activated, in any suitable manner, the switch 600 is activated such that the meter device 100 is placed in an "off" condition.

Further by way of example, the on/off switch 600 may be placed relative to a test strip platform 60 of the meter device 100, such that when a test strip 200 is placed on the test strip platform 60 and inserted in the meter device 100, a conductive portion 226 of the test strip engages the on/off switch 600, such that an electrical circuit associated with the switch 600 is closed and the meter device 100 is in an "on" condition. According to this alternative, when the conductive portion 226 of the test strip 200 is removed from the meter device 100, the electrical circuit associated with the switch 600 is open and the meter is in an "off" condition.

When the meter device is in an "on" or an "off" condition, by any means described above or whatever other suitable means is employed, power is supplied or not supplied, respectively, to the various components of the electronic system.

As described above, when light is received by the optical detector 540, it produces an electrical signal 560 that corresponds to the amount of light received. This electrical signal 560 is supplied to the microprocessor 610, as schematically shown in FIG. 8, via an operable communication therebetween. Any suitable microprocessor, such as an 8086 central processing unit chip, may be used. The electrical signal 560 may be processed, such as via an analog to digital converter, to obtain digital output, as necessary. The microprocessor is programmed to process the electrical signal 560 to obtain usable output, such as a total amount of hemoglobin in a blood sample 700, an amount of glycated hemoglobin in a blood sample 700, and ultimately, a percentage of HbA1c in the blood sample 700.

This processing typically involves the use of a calibration code, such as a calibration code associated with a test strip 200 that a user selects via a calibration selection button 40 of the meter device 100, which selection is recorded in the memory device 620 (such as an EEPROM or a RAM device, for example) of the electronic system 650 via an operable communication between the calibration selection button 40 and the memory device 620. The microprocessor 610 is programmed with a set of calibration curves, which may be stored in a memory (not shown) of the microprocessor or stored in the memory device 620 of the electronic system 650. The microprocessor 610 is in operable communication with the memory device 620, such that it can access a calibration information stored therein, process the electrical signal 560 accordingly (based on the calibration code and the set of pre-programmed calibration curves, for example), and send usable output to the memory device 620. In this way, the microprocessor 610 processes the electrical signals 560 from the optical system 550, to obtain a total amount of hemoglobin in a blood sample 700, to send this result to the memory device 620 for storage, to obtain an amount of glycated hemoglobin in the blood sample 700, to send this result to the memory device 620 for storage, and to access both results from storage for further processing, such as to obtain a percentage HbA1c result via a simple algorithm or simple ratiometric or arithmetic calculation (i.e., [(amount of glycated hemoglobin in sample)÷(total amount of hemoglobin in sample)]×100).

The system described herein is designed to provide results in the range of about 3 to about 15 or about 18 percent HbA1c, with a precision of less than or equal to about 5.0% coefficients of variation. The percentage HbA1c result may be stored in the memory device 620 for later retrieval and/or sent from the microprocessor 610 or the memory device 620 to the display device 630, via an operable communication therebetween. The memory device may be selected to have sufficient capacity to story a desired number of results, such as about 20 HbA1c percentage results, for example. The display device 630 may be the same as the display device 50 of the meter device 100, as shown in FIGS. 1-3, or it may be a different type of display device, such as a small print-out device, merely by way of example. In addition or alternatively, the result may be sent to a peripheral device, such as a computer for downloading, manipulating, and/or displaying data or an external printer for printing data, via an interface device 670 shown in FIG. 8, such as a RS-132 communication interface, having an accessible port 680 associated therewith as schematically shown in FIGS. 1-3.

A power source 570 sufficient for operating the optical system 550 or any of its various components, such as the light detector and/or any LED(s), may be part of the optical system 550 or the meter device 100, although one or more of the light detector and the LED(s) may already have one or more associated power source(s) for self-powered operation, or some other power source arrangement may be used. Further, a power source 640 sufficient for operating the electronic system 650 or any of its various components may be provided, such as a power source 640 operable communication with the on/off switch 600 of the system. Alternatively, the microprocessor 610 may have a power source sufficient for operating the electronic system 650, or some other power source arrangement may be used. Naturally, a suitable power source 660 for operating both the optical system 550 and for operating the electronic system 650 may be used, as schematically depicted in FIG. 8. Preferably, any power source used in the meter device 100 is of sufficient capacity for its purpose while being sufficiently small or compact, such as on the order of an AAA battery or a small solar cell, for example, as is consistent with a preferably small overall footprint for the meter device.

As the meter device 100 is preferably of a relatively small or user-friendly footprint, the components housed therein, such as the optical system 550 and the electronic system 650, are preferably of a size that is conducive to such a footprint and arranged in a manner that is conducive to such a footprint. For example, the footprint of the meter device 100 may be on the order of that of existing handheld HbA1c assay devices, or on the order of that of a handheld personal digital assistant (PDA) device, such as a PalmPilot PDA device commercially available from Palm, Inc. While test strips 200 and meter devices 100 of various footprints are contemplated, merely by way of example, test strips 200 having a footprint of about 2.5 inches in length, about 0.5 inches in width, and about 0.15 inches in thickness, are appropriate for use with a meter device 100 having a footprint of about 5 inches in length, about 2.5 inches in width, and about 0.5 inches in thickness.

EXAMPLES

Several examples relating to various aspects of the invention are now described.

Test strips useful for hemolysis are now described in this Example 1. A set of prototype test strips was prepared, each test strip having a sample application zone comprising a nylon membrane commercially available from Cuno Incorporated of Meriden, Conn. Another set of prototype test strips was prepared, each test strip having a sample application zone comprising a lateral flow nitrocellulose membrane commercially available from Millipore of Bedford, Mass. The sample application zone of each test strip was then treated, by coating it with, or dip-coating it in, a dilute solution (from about 0.05% to about 0.1%) of an ionic detergent (SDS) or a nonionic detergent (Triton X-100), in a volume on the order of about 2 to about 3 microliters, and drying it at room temperature for about 2 hours. A small sample of fresh whole blood, in a volume on the order of about 2 to about 3 microliters, was then applied to the treated sample application zone of each test strip. The application of the fresh blood sample to each of the test strips resulted in the hemolysis of the blood sample, as evidenced by a visual sign of sample migration, namely, an observed migration of red color from the sample application zone in a downstream direction along the test strip.

These results were also evidenced by comparision tests involving untreated test strips, comprising nylon or nitrocellulose membranes, as described above, that were not treated with a hemolysis reagent, and the prototype test strips that were treated with a hemolysis reagent. When sample of fresh whole blood were applied to the untreated test strips, there was little observable sample migration (i.e., little migration of red color along the test strip, as described above) and little measurable sample migration, as scans of the test strips using a QuadScan reflectance meter of KGW Enterprises, Inc. (associated with an operating wavelength in a range of from about 400 nm to about 855 nm) taken after sample application showed little change in the reflectance peaks or optical densities measured downstream of the sample application zones of the untreated test strips. However, when samples of fresh whole blood were applied to treated, prototype test strips, sample migration was observed, as described above, and scans of the test strips using the QuadScan reflectance meter taken after sample application showed noticeable change in the reflectance peaks or optical densities measured downstream of the sample application zones of the prototype test strips. Based on these results, the treated, prototype test strips appear to be successful vehicles for lysing the blood cells of the samples to liberate hemoglobin and allow it to migrate along the prototype test strips.

Test strips useful for eluting the hemolysed blood sample are now described in this Example 2. A set of prototype test strips was prepared, each test strip having a sample application/hemolysis zone, as described above in relation to Example 1, an eluting agent application zone upstream relative to the hemolysis zone, and a wicking membrane downstream relative to the hemolysis zone, the wicking membrane comprising a lateral flow nitrocellulose membrane commercially available from Millipore of Bedford, Mass. A small sample of fresh whole blood, in a volume on the order of about 2 to about 3 microliters, was applied to the hemolysis zone of the test strip and hemolysed, in a manner such as that set forth in Example 1. An eluting agent of phosphate buffered saline solution, of a concentration on the order of 0.01 to about 0.02 molar, was then applied to the eluting agent application zone of each test strip. For each strip, a QuadScan reflectance meter was used to obtain a reflectance reading for the total lysed hemoglobin in the hemolysis zone, and a reflectance reading in an area downstream relative to the hemolysis zone. For each strip, the application of the eluting agent to the eluting agent application zone resulted in the movement of hemoglobin downstream relative to the hemolysis zone, as evidenced by a noticeable change in the reflectance peaks or optical densities measured downstream of the sample application/hemolysis zones of the prototype test strips. Based on these results, the prototype test strips appear to be successful vehicles for removing hemoglobin from the hemolysis zones via upstream application of eluting agent and downstream presence of wicking membranes along which the liberated hemoglobin travels.

Test strips believed to be useful for capturing glycated hemoglobin from a blood sample are now described in the following Examples 3 and 4. Prototype test strips are to be prepared as described above in Example 2. For each test strip, a portion of the wicking membrane adjacent and downstream relative to the hemolysis zone is to be treated with a capture reagent to create a capture zone to capture the glycated hemoglobin as it travels away from the hemolysis zone upon elution, as described above in Example 2. For each test strip, the hemolysis reagent and the capture reagent are to be immobilized in the hemolysis zone and glycated hemoglobin capture zone, respectively. By way of example, small volumes, such as from about 1 microliter to about 2 microliters, of the hemolysis reagent and the capture reagent are applied to respective portions of the wicking membrane to create the hemolysis zone and the glycated hemoglobin capture zone of the test strip. Hemoglobin, both glycated and non-glycated, is liberated from the sample upon hemolysis, and travels away from the hemolysis zone upon elution. The capture reagent is a reagent suitable to bind the liberated glycated hemoglobin, such that it is captured in the capture zone, while allowing unglycated hemoglobin to travel further downstream relative to the capture zone. Means of capture or immobilization include physical adsorption, electrostatic interaction, chemical means, and/or binding affinity, depending on the nature of the capturing reagent relative to that of glycated hemoglobin.

In Example 3, the capture reagent is to be a reagent comprising anti-HbA1c antibodies. Such antibodies are available from various sources. The capture reagent is to be confined to, or immobilized at, the capture zone portion of the wicking membrane as described above. The capture reagent is designed to capture and immobilize the glycated hemoglobin by way of the reagent's specific affinity for glycated hemoglobin. Each test strip is to be tested to demonstrate the capture of glycated hemoglobin in the capture zone. A reflectance meter, such as the QuadScan reflectance meter, is to be used to obtain a reflectance reading for the total lysed hemoglobin in the hemolysis zone and a reflectance reading in the capture zone for each test strip. If the results show a reflectance reading associated with the capture zone that is lower than that associated with the hemolysis zone, this will demonstrate the successful capture of glycated hemoglobin by the capture reagent in the capture zone.

In Example 4, the capture reagent is to be a reagent comprising boronate ligands attached to an appropriate base unit or units of the reagent, rather than a reagent comprising anti-HbA1c antibodies as in Example 3. Such reagents are available from various sources. The capture agent is to be confined to, or immobilized at, the capture zone portion of the wicking membrane as described above. The capture reagent is designed to capture and immobilize the glycated hemoglobin by way of chemical means associated with the interaction of the capture reagent and glycated hemoglobin. Each test strip is to be tested to demonstrate the capture of glycated hemoglobin in the capture zone. A reflectance meter, such as the QuadScan reflectance meter, is to be used to obtain a reflectance reading for the total lysed hemoglobin in the hemolysis zone and a reflectance reading in the capture zone for each test strip. If the results show a reflectance reading associated with the capture zone that is lower than that associated with the hemolysis zone, this will demonstrate the successful capture of glycated hemoglobin by the capture reagent in the capture zone.

While a QuadScan reflectance meter is referenced above in relation to Examples 1-4, it should be noted that this meter is somewhat crude in that it provides readings based only on color and color intensity, operates over a broad range of wavelengths, and is not particularly sensitive. Thus, while this reflectance meter is sufficient for the Examples described herein, other suitable spectrophotometers are contemplated for use in detecting various analytes along the membrane of any test strip.

The devices, systems, and methods of the present invention are convenient means for a user, such as a patient or a health care practioner, to obtain a reading corresponding to an amount of an analytes or multiple analytes in a sample from a physiological source. Advantageously, such devices, systems and methods can be used upon the user obtaining a sample of blood, for example, using conventional means such as a lancing device, applying the sample to a test strip, and inserting the test strip in the test meter, whereupon the meter provides a result in the manner of minutes, such as from about two to about six minutes. That is, typically, the user need not precondition or manipulate the sample in any complicated or error-prone manner prior to using the test device, need not further condition or process the sample on the test strip during testing with the test device, and need not wait long for a test result.

Additionally, the devices and systems are conveniently made to be small in footprint and disposable. That is, the test meter may take the form of a handheld device having a footprint on the order of that of a handheld PDA device or an existing handheld glucose meter designed for home use. This test meter is preferably made of inexpensive parts, such that it is suitable for disposal after a few uses. The test strips designed for use with the test meter are also preferably inexpensive to manufacture, such that they are suitable for disposal after one use. The meter and one or more test strips can be provided in a kit, which kit may also comprise a device for obtaining a sample, such as a lancing device or a needle and syringe device.

The devices, systems and methods of the present invention are particularly well suited to the determination of HbA1c, such as a percentage thereof, in a blood sample. While such determinations have been described in connection with reflectance measurements, merely by way of simplicity or convenience, it will be understood that determinations based on other spectrophotometric determinations, such as transmission or absorbance of light of various wavelengths, are contemplated. The present invention provides a simple, convenient, and inexpensive means of monitoring blood glucose, particularly for users, such as diabetic patients, who must monitor blood glucose often on an on-going basis.

Various references, publications, provisional and/or non-provisional United States patent applications, and/or United States patents, have been identified herein, each of which is incorporated herein in its entirety by this reference. Various aspects and features of the present invention have been explained or described in relation to beliefs or theories or underlying assumptions or working or prophetic examples, although it will be understood that the invention is not bound to any particular belief, theory, underlying assumption, or working or prophetic example. Various modifications, processes, as well as numerous structures to which the present invention may be applicable will be readily apparent to those of skill in the art to which the present invention is directed, upon review of the specification. Although the various aspects and features of the present invention have been described with respect to various embodiments and specific examples herein, it will be understood that the invention is entitled to protection within the full scope of the appended claims.

The invention claimed is:

1. A method of treating a blood sample that comprises at least one analyte, comprising:
   providing a strip comprising a membrane, the membrane comprising
      a receiving portion for receiving the blood sample;
      a first location having a first reagent disposed thereon, wherein the first reagent lyses cells in the blood sample; and
      a second location downstream relative to the first location having a second reagent immobilized thereon, wherein the second reagent captures an analyte of the hemoglobin in the blood sample;
   providing an eluting agent disposed on the strip upstream relative to the first location, wherein the eluting agent elutes hemoglobin in the blood sample;
   applying an untreated whole blood sample to the receiving portion of the membrane;
   allowing the eluting agent to flow downstream along the membrane and contact the untreated whole blood sample, and
   detecting a level of the analyte captured at the second location.

2. The method of claim 1, wherein the membrane has a property selected from wicking functionality, capillary functionality, porosity, and any combination thereof.

3. The method of claim 1, wherein the first reagent is selected from a detergent, a hypotonic solution, and any combination thereof.

4. The method of claim 1, wherein the eluting agent is selected from a buffer, a solvent, and any combination thereof.

5. The method of claim 1, wherein the second reagent is selected from an antibody, a chemical reagent comprising at least one ligand for binding the analyte, and any combination thereof.

6. The method of claim 1, wherein the analyte is glycated hemoglobin.

7. The method of claim 1, wherein the membrane further comprises a third location downstream relative to the second location having a third reagent immobilized thereon, wherein the third reagent captures another analyte of the hemoglobin in the untreated whole blood sample.

8. The method of claim 7, wherein the third reagent is selected from an antibody, a glycoprotein, a chemical reagent comprising at least one ligand for binding the another analyte, and any combination thereof.

9. The method of claim 7, wherein the another analyte is non-glycated hemoglobin.

10. The method of claim 1, wherein providing an eluting agent comprises providing a means for containing the eluting agent.

11. The method of claim 10, wherein the means is selected from an absorbent pad, a pouch, a blister, and any combination thereof.

12. The method of claim 10, wherein allowing the eluting agent to flow comprises releasing the eluting agent from the means.

13. The method of claim 12, wherein the releasing is selected from breaking an integrity of the means, applying a pressure to the means, and any combination thereof.

14. The method of claim 1, wherein the first location is downstream relative to the receiving portion for receiving the untreated whole blood sample.

15. The method of claim 1, wherein said detecting comprises obtaining an optical signal that relates to the amount of the analyte captured at the second location.

16. The method of claim 1, wherein the eluting agent is allowed to flow downstream when a release condition is met.

17. The method of claim 1, wherein the first location is at the receiving portion for receiving the untreated whole blood sample.

* * * * *

UNITED STATES PATENT AND TRADEMARK OFFICE
CERTIFICATE OF CORRECTION

PATENT NO. : 7,670,853 B2
APPLICATION NO. : 10/533350
DATED : March 2, 2010
INVENTOR(S) : Arvind N. Jina It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 514 days.

Signed and Sealed this

Twenty-sixth Day of October, 2010

David J. Kappos
*Director of the United States Patent and Trademark Office*